United States Patent [19]

Yoshikawa et al.

[11] Patent Number: 4,620,941
[45] Date of Patent: Nov. 4, 1986

[54] THERMOCHROMIC COMPOSITIONS

[75] Inventors: Kimio Yoshikawa, Osaka; Hidetoshi Fukuo, Takarazuka; Juzo Kuroda, Yamatokoriyama, all of Japan

[73] Assignee: Sakura Color Products Corporation, Osaka, Japan

[21] Appl. No.: 666,175

[22] Filed: Oct. 29, 1984

[30] Foreign Application Priority Data

Nov. 4, 1983 [JP] Japan ................................. 58-208022
Jan. 20, 1984 [JP] Japan ..................................... 59-9352
Mar. 2, 1984 [JP] Japan ................................... 59-41009

[51] Int. Cl.$^4$ ............................................. G01N 31/22
[52] U.S. Cl. ................................. 252/408.1; 252/962; 436/2; 374/162; 116/207; 548/152
[58] Field of Search ........................... 252/408.1, 962; 374/162; 436/2, 1; 116/207

[56] References Cited

U.S. PATENT DOCUMENTS

| | | | |
|---|---|---|---|
| 3,293,055 | 12/1966 | Baum | 252/962 |
| 3,451,338 | 6/1969 | Baum | 257/962 |
| 4,138,357 | 2/1979 | Igarashi | 374/162 |
| 4,473,832 | 9/1984 | Yamato et al. | 346/209 |
| 4,507,669 | 3/1985 | Sakamoto et al. | 346/207 |
| 4,507,670 | 3/1985 | Motosugi et al. | 346/208 |
| 4,507,671 | 3/1985 | Koike et al. | 346/216 |

*Primary Examiner*—John F. Terapane
*Assistant Examiner*—S. Wolffe
*Attorney, Agent, or Firm*—Larson and Taylor

[57] ABSTRACT

A thermochromic composition comprising:
(i) at least one electron-donating organic chromogenic compound,
(ii) at least one compound serving as a color developing material and selected from thiourea and derivatives thereof, guanidine and derivatives thereof, benzothiazole, and benzothiazolyl derivatives represented by the formula

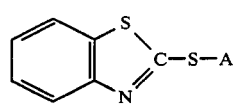

(I)

or

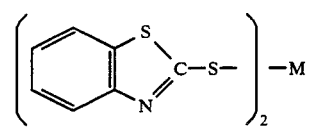

(II)

wherein A is —H,

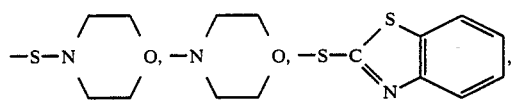

—NR$_2$, —H·NR$_3$ or —CSNR$_2$ in which R is H, C$_1$–C$_{10}$ alkyl, benzyl optionally substituted with C$_1$–C$_6$ alkyl or cyclohexyl optionally substituted with C$_1$–C$_6$ alkyl, with the proviso that all of R in —NR$_2$, —H·NR$_3$ and —CSNR$_2$ can not be H, and M is Cu, Zn, Fe, Ni, Co or Te, and (iii) and at least one compound serving as a desensitizer and selected from the group consisting of alcohols, esters, ketones, ethers, acid amides, carboxylic acids and hydrocarbons.

4 Claims, No Drawings

THERMOCHROMIC COMPOSITIONS

This invention relates to thermochromic compositions.

Thermochromic coloring compositions are known which comprise an electron-donating organic chromogenic compound (hereinafter referred to as "color former"), a color developing material (hereinafter referred to as "developer") and a desensitizer. These coloring compositions are useful as a temperature-indicating agent because they exhibit thermochromism, namely the phenomenon of reversible change of color with the change of temperature. However, conventional thermochromic coloring compositions, which chiefly contain a phenolic compound as a developer, may find limited applications because of their toxicity. Further the thermochromic coloring compositions containing a phenolic compound are likely to cause unstable thermochromism because the phenolic compounds tend to undergo oxidation and have poor resistance to sunlight.

It is an object of the present invention to provide thermochromic coloring compositions containing a substantially nontoxic developer which is not limited in use.

It is another object of the invention to provide thermochromic coloring compositions containing a chemically stable developer which enables the compositions to reversibly change their colors with the change of temperature to a sharp extent.

Other objects and features of the present invention will become apparent from the following description.

This invention provides thermochromic coloring compositions comprising:
(i) at least one electron-donating organic chromogenic compound,
(ii) at least one compound serving as a developer and selected from the group consisting of thiourea and derivatives thereof, guanidine and derivatives thereof, benzothiazole, and benzothiazolyl derivatives represented by the formula

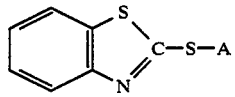
(I)

or

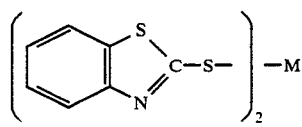
(II)

wherein A is —H,

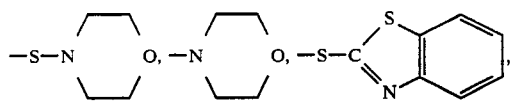

—NR$_2$, —H·NR$_3$ or —CSNR$_2$ in which R is H, C$_1$–C$_{10}$ alkyl, benzyl optionally substituted with C$_1$–C$_6$ alkyl or cyclohexyl optionally substituted with C$_1$–C$_6$ alkyl, with the proviso that all of R in —NR$_2$, —H·NR$_3$ and —CSNR$_2$ can not be H, and M is Cu, Zn, Fe, Ni, Co or Te, and
(iii) at least one compound serving as a desensitizer and selected from the group consisting of alcohols, esters, ketones, ethers, acid amides, carboxylic acids and hydrocarbons.

We conducted extensive research to overcome the foregoing drawbacks of conventional thermochromic coloring compositions and found that these drawbacks can be substantially eliminated by using as a developer at least one compound selected from the group consisting of thiourea compounds, guadinine compounds, benzothiazole, and benzothiazolyl compounds. Based on this novel finding, the present invention has been accomplished.

The components for the thermochromic compositions of this invention will be described below in detail.

I. Color former

Color formers which can be used in the present invention include any of those as used in the manufacture of conventional thermochromic coloring compositions. Examples of preferred color formers are as follows.

Triphenylmethane phthalides: Crystal Violet lactone, Malachite Green lactone, etc.

Fluorans: 3,6-diethoxyfluoran, 3-dimethylamino-6-methyl-7-chlorofluoran, 1,2-benz-o-6-diethylaminofluoran, 3-diethylamino-7-methoxyfluoran, etc.

Phenothiazines: benzoyl leuco Methylene Blue, methyl leuco Methylene Blue, ethyl leuco Methylene Blue, methoxybenzoyl leuco Methylene Blue, etc.

Indolylphthalides: 2-(phenyliminoethylidene)-3,3-dimethyl-indoline, etc.

Spiropyrans: 1,3,3-trimethyl-indolino-7'-chloro-β-naphthospiropyran, di-β-naphthospiropyran, benzo-β-naphthoisospiropyran, xantho-β-naphthospiropyran, etc.

Leucoauramines: N-acetylauramine, N-phenylauramine, etc.

Rhodamine lactams: Rhodamine B lactam, etc.

II. Developer

Given below are examples of thiourea and derivatives thereof, guadinine and derivatives thereof, benzothiazole and derivatives thereof and benzothiazolyl derivatives useful as the developer in the present invention.

Thiourea type: thiourea, methylthiourea, N,N'-dimethyl-thiourea, N-methyl-N'-methoxymethyl-thiourea, N-methyl-N'-ethoxymethyl-thiourea-N-methyl-N'-acetyl-thiourea, methyl-propyl-malonic acid-mono-(N'-methyl-thiourea), 1-methyl-dithiobiuret, N,N-dimethyl-thiourea, trimethylthiourea, tetramethylthiourea, N-methyl-N-isocaproylthiourea, N-methyl-N-propionyl-thiourea, N-methyl-N-isobutyryl-thiourea, N-methyl-N-acetyl-thiourea, N-methyl-N-valeryl-thiourea, N-methyl-N-enanthoyl-thiourea, N-methyl-N-caproyl-thiourea, N-methyl-N-undecanoyl-thiourea, ethylthiourea, N,N'-diethyl-thiourea, N,N-diethyl-thiourea, triethylthiourea, tetraethylthiourea, (2-bromoethyl)thiourea, N-methyl-N'-propyl-thiourea, N-methoxymethyl-N'-propyl-thiourea, 2,3-diiodo-propyl-thiourea, N-propyl-N'-isopropylthiourea, N-methoxymethyl-N'-isopropyl-thiourea, isopropylthiourea, N-ethoxymethyl-N'-isopropyl-thiourea, N,N'-diisopropyl-thiourea, N-methyl-N-isopropylthiourea, N,N'-dibutyl-thiourea, N-sec-butyl-thiourea, N-isopropyl-N'-tert-butyl-thiourea, N-propyl-N'-tertbutyl-thiourea, N,N'-ditert-butyl-thiourea, N-methyl-N'-tert-butyl-thiourea, 1-ethylpropyl-thiourea, N-methoxymethyl-N'-isohexyl-thiourea, dodecylthiourea, N-isopropyl-N'-dodecyl-thiourea, N,N'-didodecylthiourea, N,N'-ditetradecylthiourea, hexadecylthiourea, N,N'-dihexadecylthiourea, N,N'-dioctadecylthiourea, allylthiourea, N,N-diethyl-N'-allyl-thiourea, N,N-dibutyl-N'-allyl-thiourea, N-dioctadecyl-N'-allyl-thiourea, N,N'-diallyl-thiourea, N-allyl-N'-carboxy-thiourea, N-propyl-N'-(2-bromoallyl)-thiourea, (1-methyl-allyl)thiourea, (1-ethyl-allyl)-thiourea, N,N'-dioleyl-thiourea, oleylthiourea, N,N'-bishydroxymethylthiourea, acetylthiourea, N,N'-diacetylthiourea, monothiobiuret, 2,4-dithiobiuret, hydroxymethylthiourea, 1,5-bis-hydroxymethyl-2,4-thiobiuret, sym-diphenylthiourea, sym-di-o-tolylthiourea, N,N'-dicyclohexylthiourea, ethylenethiourea, 1-allyl-3-β-hydroxyethyl-2-thiourea, 1-phenyl-2-thiourea, N-benzoyl-thiourea, 1-(1-naphthyl)-2-thiourea, 1,1-diphenylthiourea, dimethylolthiourea, etc.

Guanidine type: guadinine and derivatives thereof such as methylguadinine, ethylguanidine, butylguanidine, 1,3-diphenylguanidine, di-o-tolylguanidine, (3-methyl-2-butenyl)guanidine, 1-benzyl-2,3-dimethylguanidine, 4-(aminobutyl)guanidine, N-(4-aminobutyl)-N-(3-methyl-2-butenyl)guanidine, [{2-(2,6-dichlorophenoxy)ethyl}amino]guanidine, [2-(3,6-dihydro-4-methyl-1(2H)-pyridinyl]guanidine, [2(hexahydro-1(2H)-azocinnyl)ethyl]guanidine, (1,4-benzodioxane-2-yl methyl)guanidine, 1-(4,5-dimethyloxazole-2-yl)-3-sulfonylguanidine, formylguanidine, 1,3-N-dipropionylguanidine, hyppurylguanidine, benzenesulfonylguanidine, p-amino-benzenesulfonylguanidine, acetylguanidine, chloroacetylguanidine, N-(aminoiminomethyl)glycine, N-(aminoiminomethyl)-N-methylglycine, N-[imino(phosphonoamino)-methyl]-N-methylglycine, guanylthiourea and the like; diguanidine and derivatives thereof such as 1,1'-[(methylethanediylidene)dinitrilo]-diguanidine and the like; diguanide and derivatives thereof such as 1,1-dimethyldiguanide, phenyldiguanide, 1-o-tolyldiguanide, 1-butyldiguanide, 1-(3,4-dichlorophenyl)-5-isopropyldiguanide, 1,1'-hexamethylenebis[5-(p-chlorophenyl)-diguanide]; and the like.

Benzothiazole type and benzothiazolyl type: benzothiazole, 2-mercaptobenzothiazole, dibenzothiazyldisulfide, 2-(N,N'-diethylthiocarbamoylthio)benzothiazole, 2-(4'-morpholinodithio)benzothiazole, 2-(N,N-dipropylthiocarbamoylthio)benzothiazole, 2-mercapto-2-thiazoline, N-cyclohexyl-2-benzothiazolylsulfenamide, N-oxydiethylene-2-benzothiazolylsulfenamide, N,N-dicyclohexyl-2-benzothiazolylsulfenamide, N-tert-butyl-2-benzothiazolylsulfenamide, N-iso-propyl-2-benzothiazolylsulfenamide, zinc salt of 2-mercaptobenzothiazole, copper salt of 2-mercaptobenzothiazole, cyclohexylamine salt of 2-mercaptobenzothiazole, etc.

III. Desensitizer

Desensitizers useful in the present invention include those commonly used in the manufacture of conventional thermochromic coloring compositions. Preferred examples thereof are as follows.

Alcohols: n-octyl alcohol, n-nonyl alcohol, n-decyl alcohol, n-lauryl alcohol, n-myristyl alcohol, n-cetyl alcohol, n-stearyl alcohol, n-eicosyl alcohol, n-docosyl alcohol, oleyl alcohol, cyclohexanol, benzyl alcohol, ethylene glycol, polyethylene glycol, trimethylolpropane, pentaerithritol, etc.

Esters: lauryl caproate, octyl caprate, butyl laurate, dodecyl laurate, hexyl myristate, myristyl myristate, octyl palmitate, stearyl palmitate, butyl stearate, cetyl stearate, lauryl behenate, cetyl oleate, butyl benzoate, phenyl benzoate, dibutyl cebacate, etc.

Ketones: cyclohexanone, acetophenone, benzophenone, dimyristyl ketone, etc.

Ethers: dilauryl ether, dicethyl ether, diphenyl ether, ethylene glycol monostearyl ether, etc.

Fatty acids: caproic acid, caprylic acid, capric acid, lauric acid, myristic acid, palmitic acid, stearic acid, arachidic acid, behenic acid, lignoceric acid, cerotic acid, palmitoleic acid, oleic acid, ricinolic acid, linoleic acid, linolenic acid, eleostearic acid, erucic acid, etc.

Acid amides: caprylic amide, capric amide, lauric amide, myristic amide, palmitic amide, stearic amide, behenic amide, oleic amide, benzamide, etc.

Hydrocarbons: aliphatic hydrocarbons such as octane, isooctane, decane, and the like; aromatic hydrocarbons such as benzene, toluene, xylene, and the like; alicyclic hydrocarbons such as cyclohexane, ethyl cyclohexane, butyl cyclohexane, and the like; solvent mixtures of these hydrocarbons commercially available as ligroin, gasoline and kerosene.

The color former, developer and desensitizer in the present invention are used in the weight ratio of usually 1:½:5 to 1:100:300, preferably 1:1:10 to 1:50:200. If the developer is present in excess, the reversible metachromatism of the composition, particularly its ability of decoloration, reduces. A lesser amount of the developer results in the decrease of color density. In excess of the desensitizer, the color density lowers, whereas a lower amount of the desensitizer impairs the decoloring ability.

When required, additives such as pigments, fillers and the like can be incorporated into the thermochromic compositions of the present invention.

We have found that when the present thermochromtic compositions include a developer thiourea and its derivative in conjunction with a thermosetting or photo-setting resin, the coating formed over a substrate can repeat a stable color forming reaction in accordance with the change of temperature. There is no particular restriction as to the kind of thermosetting or photo-setting resins as used. Examples of preferred resins are urea resin, melamine resin, polyester resin, polyurethane resin, epoxy resin, modified epoxy resin, etc. These resins can be used, when required, in combination with a curing agent such as polyamine type, organic acid type, amino resin type, phenol resin type and peroxide type. If a thermosetting or photo-setting resin is used, the proportions of the color former, developer and desensitizer are the same as above. Usually about 1 to about 100 parts, preferably about 2 to about 50 parts by weight, of the thermosetting or photo-setting resin is used per part by weight of the combination of the color former and the developer. If a thermosetting or photo-setting resin is present in large excess, the color density decreases. If the resin content is lower, the coating formed over the substrate is given a reduced adhesive property and a lower mechanical strength and can not exhibit thermochromism with improved stability.

The thermochromic compositions of the present invention can be prepared, for example, by the following processes to which, however, the production of the present thermochromic compositions is not limited.

When the present composition is used as a liquid coloring agent for writing inks and the like, a specific color former, developer and desensitizer are dissolved in a solvent. If the desensitizer is usable as a solvent in this case, the color former and the developer are dissolved in the desensitizer. Further when the present composition is employed as a solid coloring agent for crayons, pastels and the like, the components are melted with heating and stirred to obtain a homogeneous dispersion which is then shaped into a desired form and cooled. Alternatively the color former, developer and desensitizer are uniformly dispersed in a molten excipient such as microcrystalline wax, polyethylene, polypropylene or the like and the melt is shaped by casting, injection, extrusion or the like and cooled.

The thermochromic compositions of the present invention can achieve the following results.

(i) The present compositions, which contain a nontoxic or less toxic color former, are not limited in use.

(ii) The present compositions are repeatedly used for a prolonged period remains stable in thermochromism and can change their colors to a marked extent at a given temperature.

The features of the present invention will be clarified with reference to the following Examples in which parts are all by weight unless otherwise specified.

EXAMPLE 1

One part of 3,6-diethoxyfluoran, 5 parts of N-acetylthiourea and 50 parts of oleic acid were fully mixed with heating to obtain a uniform solution.

The ink-like liquid composition thus obtained was colorless at ordinary temperature, but was colored yellow when applied to the surface of paper and cooled to a temperature of 5° C. or lower. The coating on the paper, when heated to ordinary temperature, regained the original colorless state.

EXAMPLE 2

One part of Crystal Violet lactone, 25 parts of thiourea and 50 parts of cetyl alcohol were melted with heating. To the melt was added 100 parts of microcrystalline wax and the mixture was uniformly melted with heating. The resulting melt was charged into a mold for a crayon and cooled.

The solid marker thus obtained had a pale blue color at ordinary temperature, but was decolored after heating to 55° C. The marker returned to the original pale blue color after cooling.

EXAMPLE 3

One part of Crystal Violet lactone, 50 parts of sym-diphenylthiourea and 50 parts of cetyl alcohol were added to 80 parts of epoxy resin of the bisphenol A type (trademark "Epikote," product of Yuka Shell Epoxy Kabushiki Kaisha, Japan) and the mixture was uniformly kneaded. Thereto was added 20 parts of a curing agent of the polyamine type (trademark "Epikure-U," product of Shell Chemical Co., U.S.) and uniformly mixed.

The coloring composition thus obtained was applied to a glass plate and the coated plate was heated at 120° C. for 30 minutes, giving an epoxy resin coating which was blue at ordinary temperature. The coating was decolored at or above 45° C. and was excellent in adhesiveness to the glass plate and in water resistance.

EXAMPLE 4

One part of a fluoran-type dye (trademark "O-DCF," product of Hodogaya Chemical Co., Ltd., Japan) and 25 parts of thiourea were added to 50 parts of stearyl alcohol and fully mixed therewith at 80 C. The mixture was added to 100 parts of a bisphenol A-type epoxy resin (trademark "D.E.R. 337," product of The Dow Chemical Co., U.S.). Thereto were added 20 parts of a polyamine-type curing agent (the same kind as used in Example 3) and 0.1 part of an acrylate-type ultraviolet absorber (trademark "Seesorb," product of Sipuro Kasei, Japan).

The coloring composition thus obtained was applied to a ceramic plate and the coated plate was heated at 120° C. for 30 minutes, whereby a coating having an orange color at ordinary temperature was formed. The coating exhibited a property of being decolored at or above 62° C. and was outstanding in bonding strength against the ceramic plate and in water resistance.

EXAMPLE 5

One part of Crystal Violet lactone, 5 parts of allyl thiourea and 50 parts of myristyl alcohol were uniformly melted with heating and 100 parts of urethane-modified epoxy resin (trademark "Epoxy 810 ST," product of Mitsui Toatsu Chemicals Inc., Japan) was added thereto and homogeneously kneaded therewith.

The composition thus obtained was applied to paper and the coated paper was heated at 80° C. for 10 minutes and left to stand for 3 days, whereby an epoxy resin coating of blue color was produced. The coating was blue at or below 38° C., but was decolored at more than 38° C.

EXAMPLE 6

One part of Rhodamine B lactam and 25 parts of a diphenyl thiourea-type compound (trademark "Nocceler-C," product of Ouchioshinko Kagaku Kogyo Kabushiki Kaisha, Japan) were dissolved in 25 parts of cetyl alcohol and the solution was added to 200 parts of an epoxy acrylate-type photo-setting resin (trademark "UVX-N12A," product of Three Bond Co. Ltd., Japan). The mixture was uniformly kneaded.

The composition thus obtained was applied to a glass plate and was cured by radiation of ultraviolet rays, whereby a coating of deep pink color was formed. The coating was good in bonding strength against the glass plate and was decolorized at or above 55° C.

EXAMPLE 7

One part of Crystal Violet lactone, 20 parts of allylthiourea and 40 parts of stearic acid were melted with heating and was thoroughly kneaded with 100 parts of epoxy acrylate resin (trademark "Ripoxy R840," product of Showa Highpolymer Co., Ltd., Japan). To the mixture were added 1.5 parts of methyl ethyl ketone peroxide and 0.5 part of cobalt naphthenate. The composition thus obtained was applied to a glass plate and the coated plate was left to stand at room temperature for a week, whereby it turned bluish green. The coating, when heated to 75° C., was decolored.

EXAMPLE 8

One part of Crystal Violet lactone, 3 parts of Hansa Yellow 10G (product of Hoechst AG., West Germany, C.I. Pigment Yellow 3), 25 parts of sym-diphenylthiourea and 50 parts of myristic acid were mixed with heating at 135 C. The mixture was uniformly dispersed in 150 parts of an epoxy-acryl composite emulsion (trademark "Almatex-112," product of Mitsui Toatsu Chemicals Inc., Japan). The resulting ink composition was applied to wood-free paper and the coated paper was fully dried and cured by standing at room temperature for a week. The coating thus produced was green at ordinary temperature, but changed the color to yellow at 45° C. or higher.

EXAMPLE 9

One part of Crystal Violet lactone and 5 parts of phenyl diguanide were added to 20 parts of cetyl alcohol and the mixture was melted with heating to 140° C. The melt was uniformly dispersed and fed to a mold and solidified with cooling to obtain a crayon-shaped solid colorant.

The colorant thus obtained was blue at ordinary temperature, but was completely decolored when applied to paper and heated to 50° C. The change of color on the paper was reversible.

EXAMPLES 10 TO 26

Seventeen kinds of solid thermochromic coloring compositions were prepared in the same manner as in Example 9 from the components as given below in Table 1. In Table 1 and other tables to be given later, figures without parenthesis represent the amounts (part) of the components as used and the parenthesized figures refer to remarked items. The compositions reversibly changed their colors as shown below in Table 2 above and below temperature indicated in Table 2 at which the metachromatism occurred (hereinafter referred to as "metachromatic temperature).

(7) Trademark "Pigment Yellow-10 GH," product of Dainichiseika Color & Chemicals Mfg. Co., Ltd., Japan

TABLE 2

| Ex. | Metachromatic Temp. (°C.) | Color Before metachromatism (at 20° C.) | After metachromatism |
|---|---|---|---|
| 10 | 55 | Orange | Colorless |
| 11 | 35 | Pink | Colorless |
| 12 | 30 | Blue | Colorless |
| 13 | 50 | Pink | Colorless |
| 14 | 25 | Blue | Colorless |
| 15 | 40 | Orange | Colorless |
| 16 | 50 | Orange | Yellow |
| 17 | 60 | Blue | Colorless |
| 18 | 65 | Blue | White |
| 19 | 80 | Blue | Colorless |
| 20 | 75 | Red | Colorless |
| 21 | 65 | Pink | White |
| 22 | 80 | Red | Colorless |
| 23 | 45 | Blue | Colorless |
| 24 | 30 | Orange | Colorless |
| 25 | 65 | Blue | Colorless |
| 26 | 45 | Orange | Colorless |

EXAMPLE 27

One part of Crystal Violet lactone and 4 parts of N-(aminoiminomethyl)glycine were added to 25 parts

TABLE 1

| Ex. | Color Former | | Developer | | Desensitizer | | Additive | |
|---|---|---|---|---|---|---|---|---|
| 10 | Fluoran-type dye[1] | 1 | di-o-Tolylguanidine | 20 | Stearyl alcohol | 50 | — | |
| 11 | Fluoran-type dye[2] | 1 | 1,3-Diphenylguanidine | 10 | Myristyl alcohol | 30 | — | |
| 12 | Crystal Violet lactone | 1 | 1-o-Tolyldiguanide | 5 | Methyl stearate | 25 | — | |
| 13 | Fluoran-type dye[2] | 1 | Phenyldiguanide | 5 | Octadecyl stearate | 20 | — | |
| 14 | Crystal Violet lactone | 1 | 1-o-Tolyldiguanide | 2 | Caproic acid | 20 | — | |
| 15 | Fluoran-type dye[1] | 1 | Guanidine compound[4] | 5 | Lauric acid | 20 | — | |
| 16 | Fluoran-type dye[3] | 1 | 1-Butyldiguanide | 4 | Myristic acid | 25 | C.I. Pigment Yellow 3[7] | 0.8 |
| 17 | Crystal Violet lactone | 1 | Guanidine compound[5] | 5 | Palmitic acid | 20 | — | |
| 18 | Crystal Violet lactone | 1 | Guanidine compound[6] | 2 | Stearic acid | 20 | Titanium oxide | 1.0 |
| 19 | Crystal Violet lactone | 1 | Guanidine compound[6] | 2 | Stearic amide | 20 | — | |
| 20 | Fluoran-type dye[3] | 1 | 1-o-Tolyldiguanide | 1 | Caproic amide | 30 | — | |
| 21 | Fluoran-type dye[2] | 1 | 1-o-Tolyldiguanide | 10 | Caproic amide | 50 | Titanium oxide | 1.0 |
| 22 | Fluoran-type dye[3] | 1 | Guanidine compound[6] | 2 | Myristic amide | 25 | — | |
| 23 | Crystal Violet lactone | 1 | Guanidine compound[6] | 5 | Benzophenone | 20 | — | |
| 24 | Fluoran-type dye[1] | 1 | Phenyldiguanide | 5 | Dibenzyl ketone | 25 | — | |
| 25 | Crystal Violet lactone | 1 | di-o-Tolylguanidine | 10 | Diphenyl methane | 20 | — | |
| 26 | Fluoran-type dye[1] | 1 | 13-Diphenylguanidine | 10 | Dibenzyl | 30 | — | |

Remark:
[1]Trademark "O-DCF," product of Hodogaya Chemical Co., Ltd., Japan;
[2]Trademark "P-DCF," product of the same company as above;
[3]Trademark "R-DCF," product of the same company;
[4]Trademark "Nocceler-D," product of Ouchishinko Kagaku Kogyo Kabushik Kaisha, Japan;
[5]Trademark "Noccler-DT," product of Ouchishinko Kagaku Kogyo Kabushiki Kaisha, Japan;
[6]Trademark "Nocceler-BG," product of Ouchishinko Kagaku Kogyo Kabushiki Kaisha, Japan;
[7]Trademark "Pigment Yellow-10 GH," product of Dainichiseika Color & Chemicals Mfg. Co., Ltd., Japan Remark:
(1) Trademark "O-DCF," product of Hodogaya Chemical Co., Ltd., Japan;
(2) Trademark "P-DCF," product of the same company as above;
(3) Trademark "R-DCF," product of the same company;
(4) Trademark "Nocceler-D," product of Ouchishinko Kagaku Kogyo Kabushik Kaisha, Japan;
(5) Trademark "Noccler-DT," product of Ouchishinko Kagaku Kogyo Kabushiki Kaisha, Japan;
(6) Trademark "Nocceler-BG," product of Ouchishinko Kagaku Kogyo Kabushiki Kaisha, Japan;

of lauryl alcohol. The mixture was melted with heating at 120° C. and uniformly dispersed by high speed agitation. To the dispersion was added 0.5 part of C.I. Pigment Yellow-3 (Trademark "First Yellow-10GH," product of Dainichiseika Color & Chemicals Mfg. Co., Ltd., Japan). Continued agitation gave a uniform liquid coloring composition. The composition thus obtained was yellow at ordinary temperature, but turned green when applied to a glass plate and cooled to 15° C. The change of color on the plate was reversible.

EXAMPLES 28 TO 33

Liquid coloring compositions were prepared from the components as shown below in Table 3 in the same manner as in Example 27. The coloring compositions thus obtained exhibited a property of reversibly changing the color to a marked degree above and below the metachromatic temperatures indicated below in Table 4.

colors to a marked degree below and above the metachromatic temperatures as shown below in Table 5.

TABLE 5

| Ex. | Color former | | Developer | | Desensitizer | | Excipient | |
|---|---|---|---|---|---|---|---|---|
| 35 | Crystal Violet Lactone | 1 | 1-o-Tolyldiguanide | 2 | Caproic acid | 20 | Paraffin wax 135 | 90 |
| 36 | Crystal Violet Lactone | 1 | Guadinine compound[6] | 2 | Stearic amide | 20 | Polypropylene[9] | 100 |
| 37 | Fluoran-type dye[1] | 1 | di-o-Tolylguanidine | 4 | Stearyl alcohol | 10 | Polystyrene[10] | 90 |

Remark:
[1] and [6] are as described above.
[9]Trademark "Sho-allomer MA 410," product of Showa Yuka Kabushiki Kaisha, Japan
[10]Trademark "Diarex HF55," product of Mitsubishi Monsanto Kasei Kabushiki Kaisha, Japan

TABLE 3

| Ex. | Color former | | Developer | | Desensitizer | | Additive | |
|---|---|---|---|---|---|---|---|---|
| 28 | Fluoran-type dye[1] | 1 | 1-Butyldiguanide | 2 | Decyl alcohol | 20 | — | |
| 29 | Crystal Violet lactone | 1 | Phenyldiguanide | 10 | Ethyl myristate | 30 | C.I. Pigment Red 170[8] | 0.5 |
| 30 | Crystal Violet lactone | 1 | Guanidine compound[6] | 5 | Dodecyl laurate | 25 | — | |
| 31 | Fluoran-type dye[3] | 1 | 1-o-Tolyldiguanide | 5 | Dodecyl caproate | 20 | — | |
| 32 | Crystal Violet lactone | 1 | Guanidine compound[6] | 2 | Acetophenone | 25 | — | |
| 33 | Crystal Violet lactone | 1 | Guanidine compound[6] | 5 | Benzene | 20 | — | |

Remark:
[1], [3] and [6] are as above.
[8]Trademark "Permanent Red F5RK," product of Hoechst AG., West Germany

TABLE 4

| | | Color | |
|---|---|---|---|
| Ex. | Metachromatic Temp. (°C.) | Before metachromatism (at 20° C.) | After metachromatism |
| 28 | −5 | Colorless | Orange |
| 29 | 5 | Red | Violet |
| 30 | 10 | Colorless | Blue |
| 31 | −10 | Colorless | Red |
| 32 | 15 | Colorless | Blue |
| 33 | 0 | Colorless | Blue |

TABLE 6

| | | Color | |
|---|---|---|---|
| Ex. | Metachromatic Temp. (°C.) | Before metachromatism (at 20° C.) | After metachromatism |
| 35 | 25 | Blue | Colorless |
| 36 | 80 | Blue | Colorless |
| 37 | 55 | Orange | Colorless |

EXAMPLE 34

One hundred parts of polyethylene (trademark "Yukalon MV-30," product of Mitsubishi Petrochemical Co., Ltd., Japan) was melted with heating at 150° C. To the melt were added 0.5 part of Crystal Violet lactone, 2.0 parts of phenyldiguaniade and 10.0 parts of cetyl alcohol. The mixture was stirred with heating to obtain a homogeneous dispersion which was then fed into a mold and solidified with cooling to give a crayon-shaped solid colorant.

The colorant thus obtained was blue at 25° C. or lower, but turned colorless above 25° C. The metachromatism of the colorant was reversible.

EXAMPLES 35 TO 37

Solid coloring compositions were prepared from the components as indicated below in Table 5 in the same manner as in Example 34 and reversibly changed the

EXAMPLE 38

One part of Crystal Violet lactone and 4 parts of N-cyclohexyl-2-benzothiazolylsulfonamide were added to 30 parts of ethyl stearate. The mixture was melted with heating at 140° C. and uniformly dispersed with stirring. The dispersion was supplied into a mold and solidified with cooling to obtain a crayon-shaped solid colorant.

The colorant thus obtained exhibited a blue color at 20° C., but was completely decolored when applied to paper and heated at 25° C. The change of color of the colorant was reversible.

EXAMPLES 39 TO 52

Coloring compositions were produced from the components as shown below in Table 7 by following the general procedure of Example 38. The compositions obtained in Examples 52 and 53 were liquid at ordinary temperature, whereas those produced in the other Examples were solid at ordinary temperature.

Table 8 below shows the metachromatic characteristics of the compositions.

TABLE 7

| Ex. | Color former | | Developer | | Desensitizer | |
|---|---|---|---|---|---|---|
| 39 | Fluoran-type dye[1] | 1 | 2-Mercaptobenzothiazole-based developer[11] | 2 | Myristyl alcohol | 20 |
| 40 | Fluoran-type dye[3] | 1 | 2-Mercaptobenzothiazole | 4 | Oleic amide | 20 |
| 41 | Fluoran-type dye[2] | 1 | Dibenzothiazyldisulfide-based developer[12] | 5 | Benzophenone | 30 |
| 42 | Fluoran-type dye[1] | 1 | 2-Mercaptothiazole-based developer[11] | 4 | Stearic amide | 20 |
| 43 | Crystal Violet lactone | 1 | Dibenzothiazyldisulfide | 5 | Sym-diphenylethane | 30 |
| 44 | Fluoran-type dye[3] | 1 | 2-Mercaptobenzothiazole-based developer[11] | 4 | Erucic amide | 40 |
| 45 | Crystal Violet lactone | 1 | N—tert-Butyl-2-benzothiazolylsulfenamide | 5 | Stearic acid | 20 |
| 46 | Fluoran-type dye[1] | 1 | Amine salt of 2-mercaptobenzothiazole-based developer[13] | 2 | 1,4-Diphenylbutane | 20 |
| 47 | Fluoran-type dye[2] | 1 | 2-Mercaptobenzothiazole-based developer[11] | 4 | Myristic acid | 40 |
| 48 | Fluoran-type dye[1] | 1 | 2-Mercaptobenzothiazole | 3 | Dodecyl palmitate | 30 |

TABLE 7-continued

| Ex. | Color former | Developer | Desensitizer | |
|---|---|---|---|---|
| 49 | Fluoran-type dye[3] | 1 N—tert-Butyl-2-benzothiazolylsulfenamide | 5 Phenyl ether | 20 |
| 50 | Fluoran-type dye[1] | 1 Zinc salt of 2-mercaptobenzothiazole-based developer[14] | 4 Octadecyl stearate | 20 |
| 51 | Fluoran-type dye[1] | 1 Benzothiazole-based developer[15] | 10 Acetophenone | 50 |
| 52 | Fluoran-type dye[3] | 1 Amine salt of 2-mercaptobenzothiazole-based developer[13] | 4 Dodecyl caproate | 20 |

Remark:
[1], [2] and [3] are as above.
[11]Trademark "Nocceler-M," product of Ouchishinko Kagaku Kogyo Kabushiki Kaisha, Japan
[12]Trademark "Nocceler-DM," product of the same company as above
[13]Trademark "Nocceler-M-60," product of the same company
[14]Trademark "Nocceler-MZ," product of the same company
[15]Trademark "Nocceler-MDB," product of the same company

TABLE 8

| | | Color | |
|---|---|---|---|
| Ex. | Metachromatic Temp. (°C.) | Before metachromatism (at 20° C.) | After metachromatism |
| 39 | 35 | Orange | Colorless |
| 40 | 50 | Red | Colorless |
| 41 | 45 | Pink | Colorless |
| 42 | 80 | Orange | Colorless |
| 43 | 50 | Blue | Colorless |
| 44 | 60 | Red | Colorless |
| 45 | 65 | Blue | Colorless |
| 46 | 50 | Orange | Colorless |
| 47 | 50 | Pink | Colorless |
| 48 | 35 | Orange | Colorless |
| 49 | 25 | Red | Colorless |
| 50 | 50 | Orange | Colorless |
| 51 | 15 | Colorless | Orange |
| 52 | −10 | Colorless | Red |

EXAMPLE 53

One part of a fluoran-type dye (trademark"R-DCF," product of Hodogaya Chemical Co., Ltd., Japan) and 2 parts of a mercaptobenzothiazole-based developer (trademark "Nocceler-MZ," product of Ouchishinko Kagaku Kogyo Kabushiki Kaisha, Japan) were added to 40 parts of palmitic acid and the mixture was melted with heating at 120° C. and uniformly dispersed by high speed agitation. To the dispersion was added an C.I. Pigment Yellow-14 (trademark "Permanent Yellow-G," product of Hoechst AG., West Germany). Agitation was continued to obtain a homogeneous dispersion which was then fed into a mold and solidified with cooling to provide a crayon-shaped solid colorant. The colorant had a vermilon color at 20° C., but was changed to yellow when applied to a glass plate and heated to 60° C. and regained the vermilion color when cooled to 20° C.

EXAMPLES 54 to 58

Coloring compositions were prepared from the components as listed below in Table 9 in the same manner as in Example 53. Table 10 shows the metachromatic characteristics of the compositions.

TABLE 9

| Ex. | Color former | Developer | Desensitizer | Pigment | |
|---|---|---|---|---|---|
| 54 | Crystal Violet lactone | 1 Amine salt of 2-mercapto-benzothiazole-based developer[13] | 7 Cetyl alcohol | C.I. Pigment 112[18] | 0.5 |
| 55 | Fluoran-type dye[2] | 1 Zinc salt of 2-mercapto-benzothiazole-based developer[14] | 2 Linolenic dodecyl amide | 30 Titanium oxide | 1.0 |
| 56 | Crystal Violet lactone | 1 Benzothiazolyl sulfenamide-based developer[16] | 6 N—dodecyl-oleicamide | 30 C.I. Pigment Yellow-14[19] | 0.5 |
| 57 | Crystal Violet lactone | 1 2-Mercaptobenzothiazole-based developer[11] | 4 Lauric amide | 20 C.I. Pigment Yellow-14[19] | 0.5 |
| 58 | Fluoran-type dye[3] | 1 Benzothiazolyl-sulfenamide-based developer[17] | 5 Lauryl alcohol | 50 C.I. Pigment Green 41[20] | 0.5 |

Remark:
[2], [3], [11], [13] and [14] are as above.
[16]Trademark "Nocceler-CZ-G," product of Ouchishinko Kagaku Kogyo Kabushiki Kaisha, Japan
[17]Trademark "Nocceler-MSA-G," product of the same company as above
[18]Trademark "Permanent Red FGR Extra," product of Hoechst AG., West Germany
[19]Trademark "Permanent Yellow-G," product of Hoechst AG., West Germany
[20]Trademark "Hostaperm Green," product of Hoechst AG., West Germany

TABLE 10

| | | Color | |
|---|---|---|---|
| Ex. | Metachromatic Temp. (°C.) | Before metachromatism (at 20° C.) | After metachromatism |
| 54 | 50 | Violet | Red |
| 55 | 35 | Pink | White |
| 56 | 40 | Green | Yellow |
| 57 | 80 | Green | Yellow |
| 58 | 15 | Violet | Green |

EXAMPLE 59

One part of a fluoran-type dye (trademark "R-DCF," product of Hodogaya Chemical Co., Ltd., Japan), 4 parts of a mercaptobenzothiazole-based developer (trademark "Nocceler-M-60," product of Ouchishinko Kagaku Kogyo Kabushiki Kaisha, Japan), 35 parts of oleic amide, 15 parts of stearic aicd monoglyceride and 110 parts of synthetic zeolite (Trademark "Zeolum,"

product of Toyo Soda Mfg., Co., Ltd., Japan) were mixed with heating at 120° C. and uniformly dispersed. To the dispersion was added 1000 parts of polypropylene (trademark "Chissopolypro K-1008'," product of Chisso Kabushiki Kaisha, Japan). The mixture was molded by injection in a usual manner into a rod 10 mm in diameter. The shaped body was red at 25° C., but became colorless at or above 40° C. The change of color was reversible.

EXAMPLES 60 to 62

The general procedure of Example 59 was followed by use of the components as indicated below in Table 11, producing shaped bodies of coloring compositions. The shaped bodies thus obtained exhibited the thermochromic characteristics of the compositions as listed below in Table 12.

TABLE 11

| Ex. | Color former | | Developer | | Desensitizer | | Excipient | |
|---|---|---|---|---|---|---|---|---|
| 60 | Crystal Violet lactone | 1 | Dibenzothiazyl-disulfide-based developer[12] | 7 | Diphenylmethane | 30 | Polypropylene[21] | 350 |
| 61 | Crystal Violet lactone | 1 | 2-Mercaptobenzothiazole-based developer[11] | 4 | Stearic amide Dodecylbenzene | 20 10 | Polystyrene[22] | 300 |
| 62 | Fluoran-type[2] | 1 | Benzothiazolylsulfenamide-based developer[16] | 6 | Capric amide | 20 | Polyethylene[23] | 300 |

Remark:
[2], [11], [12] and [16] are as above.
[21]Trademark "Tokuyama Polypro MS 240," product of Tokuyama Soda Co., Ltd., Japan
[22]Trademark "Stylon 605," product of Asahi Chemical Industry Co., Ltd., Japan
[23]Trademark "Yukalon," product of Showa Yuka Kabushiki Kaisha, Japan

TABLE 12

| | | Color | |
|---|---|---|---|
| Ex. | Metachromatic Temp. (°C.) | Before metachromatism (at 20° C.) | After metachromatism |
| 60 | 25 | Blue | Colorless |
| 61 | 40 | Blue | Colorless |
| 62 | 65 | Pink | Colorless |

EXAMPLE 63

One part of Crystal Violet lactone, 2 parts of diphenylthiourea and 40 parts of ethyl stearate were fully stirred with heating to obtain a homogeneous solution.

The ink-like liquid composition thus obtained was colorless at ordinary temperature, but was colored blue when cooled to below 10° C.

EXAMPLE 64

The general procedure of Example 63 was repeated, producing a composition comprising 1 part of NC-O (trademark, fluoran-type dye of Hodogaya Kagaku Kogyo Kabushiki Kaisha, Japan), 2 parts of diphenylthiourea and 20 parts of N-oleyl palmitic amide. The composition thus obtained was of a bright orange color at ordinary temperature, but turned colorless at 70° C. or higher.

EXAMPLE 65

A homogeneous composition was produced in the same manner as in Example 63 from 1 part of Crystal violet lactone, 5 parts of ethylthiourea and 50 parts of benzophenone. The composition was blue at ordinary temperature, but turned colorless at 45° C. or higher.

EXAMPLE 66

A homogeneous composition was prepared in the same manner as in Example 63 from 1 part of NC-R (trademark, fluoran-type dye of Hodogaya Chemical Co., Ltd., Japan), 4 parts of diphenylthiourea and 25 parts of didecyl ether.

The ink-like liquid composition was colorless at ordinary temperature, but was colored red at or below 14° C.

EXAMPLE 67

A homogeneous composition was prepared in the same manner as in Example 63 from 1 part of NC-R, 2 parts of allylthiourea and 20 parts of diphenylmethane.

The ink-like liquid composition thus obtained was red at ordinary temperature, but turned colorless at 45° C. or higher.

EXAMPLE 68

The composition (23 parts) obtained in Example 64 was mixed with 50 parts of Yuban 10S-60 (trademark, butylated urea resin of Mitsui Toatsu Chemicals Inc., Japan) and 75 parts of Epikote 828 (trademark, epoxy resin of Yuka Shell Epoxy Kabushiki Kaisha, Japan). Thereto was further added 20 parts of Epikure U (trademark, polyamine-type curing agent of Shell Chemical Co., Ltd., U.S.). The mixture was applied to a tinplate sheet and heated to 120° C. for 30 minutes, giving a coating which was of an orange color at ordinary temperature but which turned colorless at 70° C. or higher.

EXAMPLE 69

One part of NC-R, 3 parts of diphenylthiourea and 50 parts of myristyl alcohol were fully stirred with heating to obtain a homogeneous composition. Fifty-four parts of the composition thus obtained was mixed with 108 parts of Olester XRA-1319 (trademark, polyester-type ultraviolet-setting resin of Mitsui Toatsu Chemicals Inc., Japan) and 3 parts of benzophenone. The ink-like liquid composition thus obtained was applied to a glass plate and cured by ultraviolet rays, thereby producing a coating which was red at ordinary temperature but which turned colorless at 40° C. or higher.

EXAMPLE 70

A uniform composition was prepared by mixing together with heating 1 part of Crystal Violet lactone, 5 parts of diphenylthiourea and 50 parts of cetyl alcohol. Fifty-six parts of the composition thus obtained was mixed with 224 parts of Sanplain C-180 (trademark, polyurethane of Sanyo Kasei Kabushiki Kaisha, Japan).

The ink-like liquid composition thus produced was applied to a rubber sheet and the coated sheet was left to stand at ordinary temperature for 24 hours. The coating thus formed was blue at ordinary temperature, but turned colorless at 48° C. or higher.

We claim:

1. A thermochromic composition comprising:

(i) at least one electron-donating organic chromogenic compound, (ii) at least one compound serving as a color developing material and selected from guanidine and derivatives thereof, benzothiazole, and benzothiazolyl derivatives represented by the formula

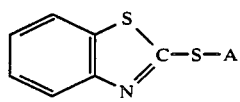
(I)

or

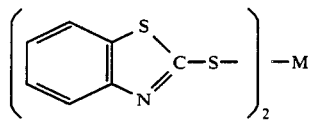
(II)

wherein A is —H,

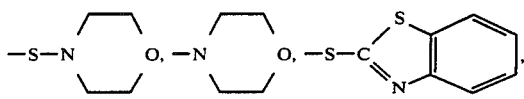

—NR$_2$, —H·NR$_3$ or —CSNR$_2$ in which R is H, C$_1$–C$_{10}$ alkyl, benzyl optionally substituted with C$_1$–C$_6$ alkyl or cyclohexyl optionally substituted with C$_1$–C$_6$ alkyl, with the proviso that all of R in —NR$_2$, —H·NR$_3$ and —CSNR$_2$ can not be H, and M is Cu, Zn, Fe, Ni, Co or Te, and (iii) at least one compound serving as a desensitizer and selected from the group consisting of alcohols, esters, ketones, ethers, acid amides, carboxylic acids and hydrocarbons.

2. A thermochromic composition as defined in claim 1 in which the electron donating organic chromogenic compound is at least one compound selected from triphenylmethane phthalides, fluorans, phenothiazines, indolyl phthalides, spiropyrans, leucoauramines and Rhodamine lactams.

3. A thermochromic composition as defined in claim 1 which contains 0.5 to 100 parts by weight of the color developing material and 5 to 300 parts by weight of the desensitizer, per part of the electron-donating organic chromogenic compound.

4. A thermochromic composition as defined in claim 3 which contains 1 to 50 parts by weight of the color developing material and 10 to 200 parts by weight of the desensitizer, per part of the electron-donating organic chromogenic compound.

* * * * *